US008760642B2

(12) United States Patent
Hori et al.

(10) Patent No.: US 8,760,642 B2
(45) Date of Patent: Jun. 24, 2014

(54) SUBSTRATE INSPECTION APPARATUS AND MASK INSPECTION APPARATUS

(75) Inventors: Zenta Hori, Kanagawa (JP); Haruhiko Kusunose, Kanagawa (JP); Koichi Moriizumi, Kanagawa (JP)

(73) Assignee: Lasertec Corporation, Kanagawa (JP)

( * ) Notice: Subject to any disclaimer, the term of this patent is extended or adjusted under 35 U.S.C. 154(b) by 200 days.

(21) Appl. No.: 13/293,305

(22) Filed: Nov. 10, 2011

(65) Prior Publication Data

US 2012/0287424 A1    Nov. 15, 2012

(30) Foreign Application Priority Data

May 13, 2011    (JP) .................................. 2011-107723

(51) Int. Cl.
*G01N 21/88*    (2006.01)
(52) U.S. Cl.
USPC .................. 356/237.2; 356/237.4; 250/201.3
(58) Field of Classification Search
USPC ............... 356/237.1–237.5; 250/201.2–201.4
See application file for complete search history.

(56) References Cited

U.S. PATENT DOCUMENTS

| | | | | |
|---|---|---|---|---|
| 5,042,951 | A | * | 8/1991 | Gold et al. ..................... 356/369 |
| 5,604,344 | A | * | 2/1997 | Finarov ....................... 250/201.3 |
| 5,892,579 | A | * | 4/1999 | Elyasaf et al. ............. 356/239.8 |
| 6,674,522 | B2 | * | 1/2004 | Krantz et al. .............. 356/237.1 |
| 7,835,015 | B1 | | 11/2010 | Wright et al. |
| 2002/0080346 | A1 | * | 6/2002 | Vaez-Iravani et al. ...... 356/237.2 |
| 2003/0142398 | A1 | * | 7/2003 | Leblans ........................ 359/383 |
| 2005/0146714 | A1 | * | 7/2005 | Kitamura et al. ........... 356/237.2 |
| 2007/0252984 | A1 | * | 11/2007 | Van Beek et al. ............. 356/311 |
| 2007/0291280 | A1 | * | 12/2007 | Rembe et al. ................. 356/516 |
| 2009/0310147 | A1 | * | 12/2009 | Miki ............................. 356/624 |

FOREIGN PATENT DOCUMENTS

| | | | |
|---|---|---|---|
| JP | 2004-069795 | * | 3/2004 |
| JP | 2009-139447 A | | 6/2009 |

OTHER PUBLICATIONS

European Search Report issued on Mar. 14, 2013 in counterpart European application.
Korean Office Action issued on Jul. 25, 2013 in counterpart Korean application.
Korean Office Action issued on Dec. 26, 2013 in counterpart Korean application, with the English translation of relevant portion.

* cited by examiner

*Primary Examiner* — Hoa Pham
(74) *Attorney, Agent, or Firm* — Carrier Blackman & Associates, P.C.; Joseph P. Carrier; Michael J. McCandlish

(57) ABSTRACT

Substrate inspection apparatus, in which the acquisition of the inspection data for a defect and the acquisition of the focus data of the objective lens are performed in parallel, includes an autofocus apparatus for controlling position of the objective lens along its optical axis. The autofocus apparatus includes a focus error detection unit and a focus control signal generation unit for generating a focus control signal for controlling the position of the objective lens for each scan line using a focus data signal composed of an objective position signal or the objective position signal to which a focus error signal is added. When "i" is assumed as a positive integer and "m" is as a natural number, the focus data signal which was acquired during the scanning period of i-th scan line is used to produce the focus control signal used to scan the (i+2m)-th scan line.

27 Claims, 6 Drawing Sheets

SUBSTRATE INSPECTION APPARATUS AND MASK INSPECTION APPARATUS

TECHNICAL FIELD

The present invention relates to a substrate inspection apparatus and a mask inspection apparatus in which a position of an objective lens is automatically controlled.

BACKGROUND ART

As a mask inspection apparatus which detects a defect existing on a photomask, the mask inspection apparatus which captures a reflected image or a transmitted image of the photomask and compares the captured image with a reference image so as to detect the defects is used in practice. In order to accurately detect the defect in the mask inspection apparatus, it is important to precisely control a focal point of the objective lens which focuses the reflected light or the transmitted light emitted from the photomask. For instance, when the focal point of the objective lens deviates from the surface of the photomask, the captured image of the photomask becomes blurred, and therefore the problem arises that a number of false defects are detected frequently. Furthermore, the mask patterns formed on the photomask become finer and the line width of the pattern is designed so as to be around 200 nm. Therefore, it is strongly demanded that the focus control of the objective lens is performed more accurately in accordance with the refinement of the patterns.

A substrate of the photomask has inevitable deflection or flexure. Although a combination of an air slider and a linear motor is usually used as a driving device for driving a stage for supporting the mask, a minute displacement along the Z axis occurs in the stage during its movement. Accordingly, in the mask inspection apparatus, an autofocus system for controlling a position of the focal point of the objective lens along an optical axis is used in order to correspond to the deflection of the photomask and the undesirable movement of the stage.

As a conventional autofocus system, it is well-known that the distance between the focal point of the objective lens and the surface of the photomask is detected as a focus error signal and that the position of the objective lens along its axis is feedback controlled using the detected focus error signal. In this known autofocus system, a focus detector for detecting the deviation between the focal point of the objective lens and the surface of the photomask by for example an astigmatic method is used, and the focus error signal is produced using the output signal form the focus detector. During the scanning of the photomask, feedback control by use of the focus error signal is performed so that the deviation between the focal point of the objective lens and the surface of the photomask becomes zero.

As another substrate inspection apparatus, a reticle inspection apparatus in which a height distribution of an upper surface of the reticle is measured to form a three dimensional topographical map of the whole surface of the reticle prior to the inspection and the position of the objective lens is controlled using the three dimensional topographical map has been known (for example, see PLT 1). In this known inspection apparatus, after the three dimensional topographical map of the whole surface of the reticle is produced, the inspection of the reticle is performed, and the position of the objective along its optical axis is controlled using the topographical map during the inspection.

PLT1: U.S. Pat. No. 7,835,015

SUMMARY OF INVENTION

Technical Problem

In the substrate inspection apparatus in which the prior autofocus system of the feedback control type is equipped, a delay relative to the focus error signal occurs in a servo system, and there is a limit in performing the accurate autofocus controlling. Furthermore, since various patterns are formed on the surface of the photomask, diffracted light and scattered light caused by the patterns formed on the substrate is made incident upon a light detector of the autofocus apparatus. Such diffracted light and scattered light appears as a noise component of high frequency that is included in the focus error signal. Therefore, when the focus error signal is just used to perform feedback control, undesired influence caused by the diffracted light and the scattered light appears in the focus control and the focal point of the objective lens deviates from the surface of the photomask, and thereby the problem arises that an indistinct image is captured.

In the above-mentioned substrate inspection apparatus, the three dimensional topographical map of the surface of the reticle is produced and the focal point of the objective lens is controlled based on the produced three dimensional topographical map. Such controlling method achieves an advantage in which the objective lens is accurately controlled in comparison with the feedback controlling. However, it is necessary to scan the whole inspection area ahead of the scanning for performing of detection of the defects in order to form the topographical map. That is, twice scanning operations of the scanning for forming of the topographical map and the scanning for detecting of the defects are necessary. As the result of this, the problem arises of the inspection time being longer and the throughput of the inspection being degraded.

An object of the present invention is to realize a substrate inspection apparatus in which the acquisition of the defect detection data and the acquisition of the control data which are used for controlling the focal point of the objective lens are performed in parallel. Another object of the present invention is to realize a substrate inspection apparatus in which the influence caused by the diffracted light and the scattered light is reduced. Furthermore, still another object of the invention is to provide a mask inspection apparatus in which the acquisition of the defect detection data and the acquisition of the control data which are used for controlling the focus of the objective lens are performed in parallel. Furthermore, still another object of the invention is to realize a mask inspection apparatus in which the influence caused by the diffracted light and the scattered light is reduced. Still another object of the invention is to realize a mask inspection apparatus which can sufficiently correspond to the refinement of the patterns formed on the substrate.

Solution to Problem

The substrate inspection apparatus according to the invention comprising a stage for supporting a substrate to be inspected, an illumination optical system for projecting an illumination beam toward the substrate, an objective lens for focusing transmitted light through the substrate or reflected light by the substrate, light detection means for receiving the transmitted light or the reflected light emitted from the objective lens, a driving device for driving the objective lens along its optical axis, a position sensor for detecting a position of the objective lens along its optical axis to produce an objective position signal for representing the position of the objective lens along its optical axis, and an autofocus system for controlling the position of the objective lens along its optical axis during the inspection of the substrate, wherein said stage or the objective lens moves in a first scan direction, a second scan direction whose scanning direction is opposed to that of the first scan direction and a third direction which is perpendicular to the first and second scan directions in a zigzag fashion to scan on scan lines which respectively extend in the first or second scan direction and are set in the third direction one by one, and the inspection data for the substrate and the position data of the objective lens along its optical axis are acquired for each scan line during the scanning of respective scan lines, and wherein said autofocus system comprises focus error detection means for detecting a focus error between the objective lens and a surface of the substrate so as to generate a focus error signal, and focus control signal generation means for generating a focus control signal which is used to control the position of the objective lens along its optical axis using a focus data signal comprising of the objective position signal or the objective position signal to which the focus error signal is added, and wherein when "i" is assumed as a positive integer and "m" is assumed as a natural number, the focus control signal which is used to scan an (i+2m)-th scan line is formed using the focus data signal which was acquired during the scanning period of an i-th scan line.

According to the invention, the acquisition of the defect detection data for the substrate and the acquisition of the focus data of the objective lens are performed in parallel. The focus control signal for controlling the position of the objective lens along its optical axis during the inspection is generated using a target value which is produced by use of focus data signal composed of the objective position signal which was acquired during the inspection or the objective position signal to which the focus error signal is added. The target value forming means for producing the target value include smoothing means for smoothing the focus data signal in order to produce the target value using the smoothed focus data signal. In this case, since the focus control signal is generated by use of the smoothed target value, situation that an incorrect focus control caused by the patterns is carried out is prevented, even if the diffracted light and the scattered light caused by the patterns formed on the surface of the substrate strike the focus detector during the scanning. Therefore, even if the patterns formed on the surface of the substrate become finer or complicated, the focus controlling that is not affected by the patterns can be performed.

Further, according to the invention, when the target value which is used to generate the focus control signal is produced, the focus data signal which was acquired from two scan lines earlier is used. That is, the target value which is produced using the focus data signal acquired during the scanning of the i-th scan line is used to generate the focus control signal which is used to scan the (I+2m)-th scan line ("m" is a natural number.) rather than (i+1)-th scan line. The reason for this is as follows.

(1) The line width of patterns formed on the surface of photomasks becomes finer to be around 100 µm, and thus it is demanded that more accurate focus control is carried out in the mask inspection apparatus for detecting the defects existing on the photomask. Therefore, most of X-Y stages are driven by a combination of an air slider and a linear motor. However, even if such driving mechanism is used, yawing and pitching behaviors occur in the moving stage while the stage scans the scan line. Such yawing and pitching behaviors correlate to a moving direction of the stage. Therefore, in case that the stage moves on the same scan line in the opposite directions, the form and behavior of the stage do not correspond to each other and differences in the form and behavior between the moving directions occur. Such differences are included in the focus error signal. That is, when the stage moves on the scan line in a first scan direction, the focus errors detected by the focus detector include a displacement of the surface of the photomask along the optical axis and a displacement of the moving stage along the optical axis. Therefore, when the stage moves on the same scan line in a second scan direction opposite to the first direction, the focus errors detected by the focus detector differ from those detected when the stage moves in the first scan direction. This is because, the displacements that occur in the moving stage along the optical axis are different in each direction, even if the displacements of the surface of the photomask are the same. On the other hand, in an optical apparatus in which the stage moves in a zigzag fashion, a scan direction of a i-th scan line and that of a (i+2m)-th scan line correspond to each other ("m" is a natural number). Therefore, if the focus control signal which is produced using the focus data signal acquired during the scanning of the i-th scan line is used to scan a (i+2)-th scan line or a (i+4)-th scan line, the stage moves in the same scan direction and thus a focus control signal in which the influence of the pitching and yawing is substantially reduced can be obtained. As the result of this, it is possible that more accurate focus control is carried out.

(2) Since the focus data signal outputted from the focus detector includes the diffracted light and scattered light component caused by the patterns formed on the surface of the photomask, it is desired to smooth the acquired focus data signal or focus error signal. However, considerable processing time is necessary in order to perform the smoothing process. In this circumstance, if the focus control signal is produced using a focus data acquired during the scanning of an adjacent scan line, the problem arises that the number of the sampling data which are used to produce the focus control signal is substantially limited. On the contrary, if the number of the sampling data which are used for focus control is increased, the accuracy of the focus control is improved, but the processing time required for the smoothing process becomes longer and thereby the problem arises that the throughput of the inspection is decreased. Because, it is necessary to keep the stage in rested state during the smoothing process. On the contrary, if the focus control signal which is used to scan the (i+2)-th scan line is produced using the focus data signal acquired during the scanning of the i-th scan line, the smoothing process for this focus data signal can be performed during the next scanning period of the (i+1)-th scan line in which the stage moves in the opposite scan direction. Therefore, as the processing time required for the smoothing process, the scanning time of one scan line can be assigned and thus the number of the sampling data can be considerably increased. Furthermore, a complicated smoothing process which requires considerable longer operation time can be performed and thereby the accuracy of the focus control is remarkably improved.

(3) When the focus control signal is produced using the focus data signal acquired during the scanning period of the adjacent scan line, the arrangement sequence of the data is reverse, and thus it is necessary to rearrange the acquired focus data signal. As the result of this, the problem arises that the signal processing becomes complicated. On the contrary, when the focus data signal acquired during the scanning period of the i-th scan line is used to produce the focus control signal used to scan the (i+2m)-th scan line, the arrangement sequence of the data corresponds to each other, and thus the rearrangement process of the acquired focus data signal is unnecessary.

Based on the above mentioned advantages, according to the present invention, the focus data signal which was acquired during the scanning period of the i-th scan line is used to produce the focus control signal which is to be used to scan the (i+2m)-th scan line. Therefore, according to the invention, a focus data signal is acquired by scanning an i-th scan line, the acquired focus data signal is smoothed during the next scanning period of an (i+1)-th scan line, and the smoothed focus data signal is used to produce a focus control signal which is to be used to scan an (i+2)-th scan line. Furthermore, when the focus control for the (i+2)-th scan line is performed using the focus data signal acquired during the scanning period of the i-th scan line, there is formed a space corresponding to two scan lines. But, such space is around 200 µm, and it is verified by the inventor' experiment that such space does not affect the inspection accuracy.

As the focus data signal which is used to produce the target value, an objective position signal which represents a position of an objective lens along its optical axis or the objective position signal to which a focus error signal is added.

According to the invention, as a smoothing process, various smoothing processes can be performed, and for example moving average process can be carried out. Alternatively, low pass filter processing can be carried out. In this case, a cut-off frequency may be determined based of the density of the patterns formed on the photomask. Further, as another smoothing process, a difference value between adjacent data values is detected, and when the detected difference value exceeds a predetermined threshold level, such data values are eliminated and a linear interpolation is performed.

Advantageous Effects of Invention

According to the present invention, the focus control signal is produced using the focus data signal which was acquired during the scanning period in which the stage moves in the same scanning direction, such that a focus control signal may be formed which includes only a small error component caused by the stage movement, and thereby more accurate focus control can be carried out. Further, since the focus data signal which was acquired during the scanning of the i-th scan line is used to produce the focus control signal used for scanning the (I+2)-th scan line, the smoothing process can be performed during the scanning of the (I+1)-th scan line and thereby the throughput of the inspection can be improved. Furthermore, the target value which is used to produce the focus control signal is formed using the smoothed focus data signal, thereby minimizing the effect of scattered light and diffracted light on the focus control, even if complicated and dense patterns are formed on the substrate.

EMBODIMENTS OF INVENTION

Figure 1:
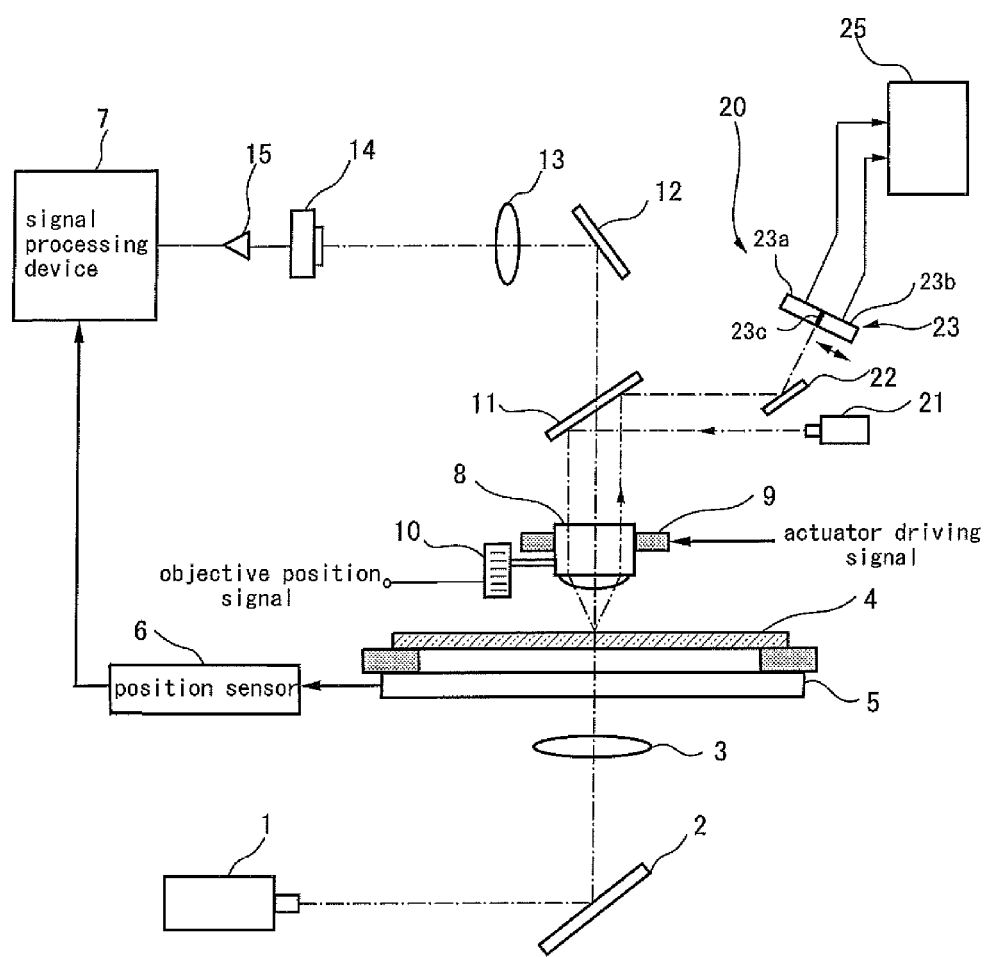
FIG. 1 is a view showing one example of an optical system of a mask inspection apparatus according to the present invention.

FIG. 1 is a line drawing showing one example of an optical system of the substrate inspection apparatus according to the present invention. The substrate inspection apparatus according to the invention can be used for inspection of various substrates such as a photomask, mask blanks, semiconductor substrate and glass substrate. In the present example, as the substrate to be inspected a photomask is used, and a mask inspection apparatus of a transmission type which detects a defect existing on the photomask using transmitted light will be explained. Further, the present invention can be applied to an inspection apparatus of a reflection type which detects the defects using reflected light from the photomask and an inspection apparatus which detects the defects based on a composite image consisting of a transmitted image and a reflected image of the photomask. Further, the present invention is applicable to various inspection apparatus in which image data of the substrate to be inspected are acquired by an objective lens.

An illumination beam for inspection is projected from an illumination light source 1. As the illumination light source, for example a laser for producing an illumination beam whose wavelength is 213 nm can be used. The illumination beam emitted from the illumination light source 1 is reflected by a total reflection mirror 2, is collected by a condenser lens 3, and is made incident upon the photomask 4. The photomask to be inspected can be photomasks of various types such as a halftone mask and a binary mask. The photomask 4 is arranged on a stage 5. The stage 5 is comprised of a X-Y stage which can move along X direction and Y direction which is perpendicular to X direction. During the inspection, the stage 5 moves along X and Y directions in a zigzag fashion, so that the photomask 4 is scanned by the illumination beam in a zigzag fashion. The position information of the stage in X and Y directions is detected by a position sensor 6, and the position information of the stage is supplied to the signal processing device 7.

The illumination beam transmitted through the photomask 4 is focused by the objective lens 8. The objective lens 8 is supported such that it can move along its optical axis. An actuator 9 is connected to the objective lens, and then the objective lens 8 moves along its optical axis by driving the actuator. As an actuator, various type actuators can be used. In the present example, the actuator includes a piezo element and the position of the objective lens along its optical axis is controlled by a driving voltage signal applied to the piezo element. To the objective lens 8, a position sensor 10 which detects the position of the objective lens along its optical axis is also connected. In the present example, as the position sensor 10, a combination of a Z axis scale and a linear encoder is used, and the position of the objective lens along the optical axis is detected using the output signal from the linear encoder.

The transmitted beam focused by the objective lens 8 is transmitted through a half mirror 11 and strikes a total reflection mirror 12. Then, the transmitted beam reflected by the total reflection mirror 12 is imaged on an imaging device 14 through an imaging lens 13. As the imaging device 14, for example a TDI sensor can be used. The image signal outputted from the imaging device 14 is then amplified by an amplifier 15 and is supplied to the signal processing device 7. The signal processing device 7 forms a transmitted image of the photomask using the image signal outputted from the imaging device 14, and detects the defects existing on the photomask by a die to die comparison method, for example. Furthermore, as a defect detecting method, it is possible to use die to database comparison method.

Figure 2:
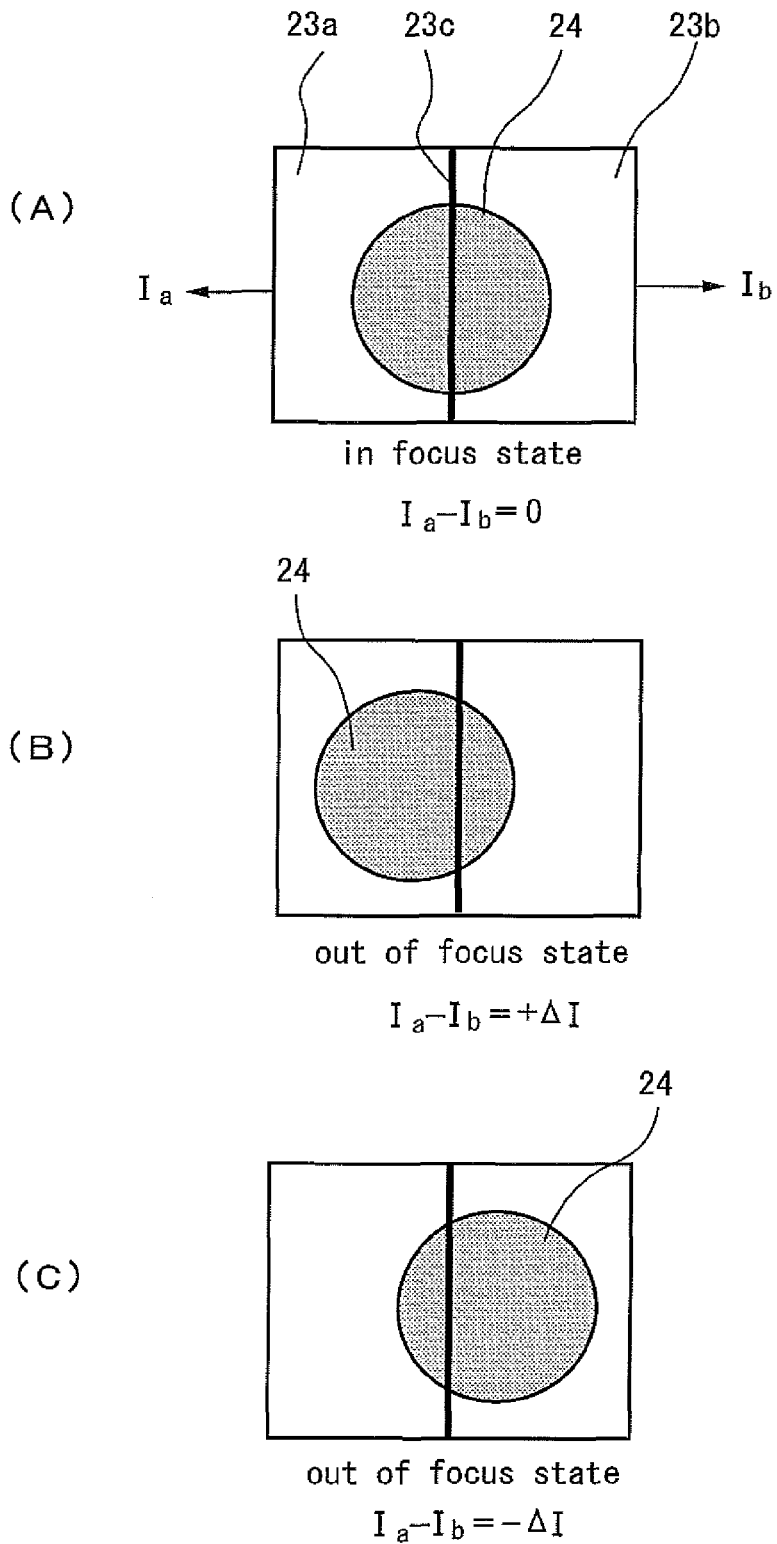
FIG. 2 is a view showing a moving fashion of a light spot formed on light detection means.

In order to control the position of the objective lens 8 along its optical axis, an autofocus system 20 is used. The autofocus system comprises a light source 21 for emitting a light beam. The light beam emitted from the light source 21 is reflected by the half mirror 11, and is made incident on the photomask 4 through the objective lens 8. The reflection beam reflected by the surface of the photomask passes through the objective lens 8, is reflected by the half mirror 11 and a total reflection mirror 22, and is made incident on a light detector 23. Then, the reflected beam forms a light spot on the light detector 23. The light detector 23 operates as a focus detector for detecting the focusing state of the objective lens relative to the surface of the photomask. As the focus detector, it is possible to use focus detectors of various types. As the focus detector, a line sensor comprising a plurality of light receiving elements which are arranged in a direction of the movement of the light spot can be used. As shown in FIG. 2, in the present example, as the focus detector, a light detector of two division type having two photodiodes 23a and 23b as well as a division line 23c formed between the two photodiodes is used. The reflected beam reflected by the surface of the photomask strikes the light detector 23 through the objective lens 8, and forms a circular light spot 24 on the light detector 23. The light spot 24 moves in a direction perpendicular to the division line 23c responsive to the focus error. Therefore, two photodiodes 23a and 23b are arranged in the direction of the movement of the light spot 24. The output signals Ia and Ib outputted from the photodiodes 23a and 23b are supplied to a processor 25 and are used to produce a focus error signal representing the deviation between the focal point of the objective lens and the surface of the photomask.

When the surface of the photomask is displaced along the optical axis by, for example, flexure or deflection inevitably caused in the photomask, the incident point of the light beam on the photomask is also displaced. With such displacement, the light spot formed on the light detector 23 moves along in a direction of one of the arrows as shown in FIG. 2. FIG. 2 (A) denotes the state of the light spot 24, when the focal point of the objective lens is positioned on the surface of the photomask 23, that is, the objective lens is focused relative to the surface of the photomask. When the focal point of the objective lens is positioned on the surface of the photomask, the center of the light spot 24 is positioned on the division line 23c. In this case, the intensity of the output signals Ia and Ib become equal to each other and the difference between the output signals Ia and Ib becomes zero. On the other hand, if the surface of the photomask displaces along the optical axis partially, the incident point of the light beam on the surface of the photomask also displaces. With such displacement of the incident point, the position of the light spot 24 formed on the light detector is also displaced depending on the displacement of the surface of the photomask along the optical axis.

Such state is denoted in FIG. 2B and FIG. 2C. As one example, FIG. 2B shows the state of the light spot when the focal point of the objective lens displaces above the surface of the photomask, and FIG. 2C shows the state of the light spot when the focal point of the objective lens displaces below the surface of the photomask. When the focal point of the objective lens is displaced above the surface of the photomask, the intensity of the output signal from the first photodiode 23a increases and the intensity of the output signal from the second photodiode 23b decreases. When the focal point of the objective lens deviates below the surface of the photomask, the intensity of the output signal from the first photodiode 23a decreases and the intensity of the output signal from the second photodiode 23b increases. Therefore, the deviation between the focal point of the objective and the surface of the photomask is detected by detecting the difference in intensity between the output signals from two photodiodes 23a and 23b. Furthermore, in the present example, as the light detector, the photodiode which is divided into two portions is used, however it is possible to use a line sensor comprising a plurality of light receiving elements which are arranged in the direction of the movement of the light spot 24.

Figure 3:
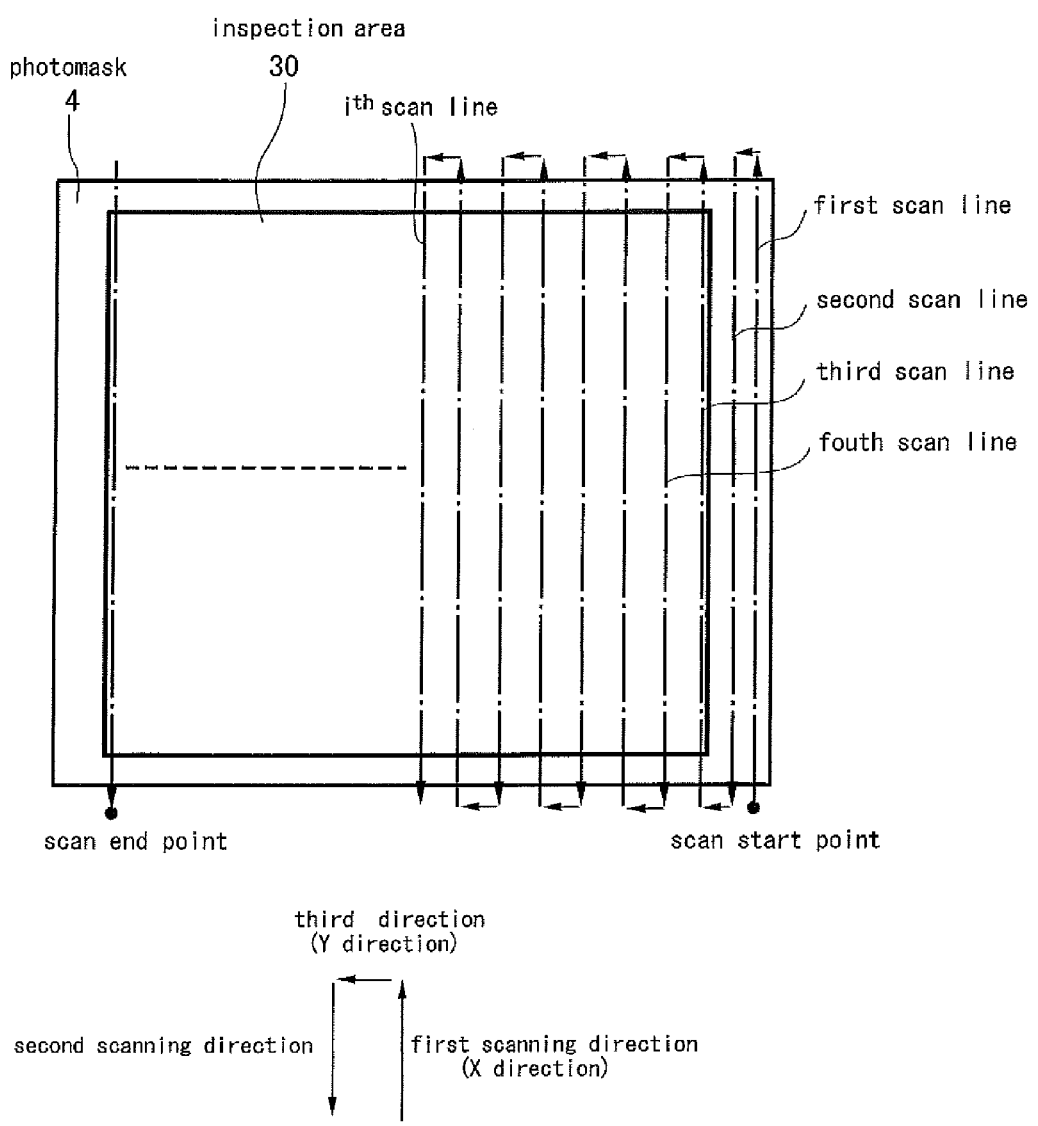
FIG. 3 is a view showing a scanning fashion of the mask inspection system.

Then, a scanning method of the photomask will be explained. In the present example, the stage 5 holding the photomask moves in the X and Y directions in a zigzag fashion, and thereby the surface of the photomask is scanned by the illumination beam for detecting defects and by the light beam for autofocusing. FIG. 3 is a view showing the relation between the photomask, an inspection area which is set to the photomask and scan lines which are set to the inspection area. Firstly, the inspection area 30 to be inspected is set on the photomask. The inspection area 30 is comprised of a rectangular region defined by the X and Y directions. The X direction is assumed as a first scan direction, and a direction whose scanning direction is opposite to that of the first scan direction is assumed as a second scan direction, and the Y direction which is perpendicular to the first and second scan directions is assumed as a third direction. The stage for holding the photomask moves in the first scan direction so that the photomask is scanned by the illumination beam for inspection and by the light beam for autofocusing, and then moves a given span length in the third direction, and then moves in the second scan direction whose scanning direction is opposed to the first direction. Therefore, the photomask is scanned by the illumination beam for inspection and by the light beam for autofocusing in a zigzag fashion. The moving amount of the third direction is defined by a field of the imaging device and is set to 100 μm, for example.

According to the invention, scan lines which respectively extend in the first and second scan directions are set. The image data for inspection (inspection data) are acquired for each scan line, and the focus error signal representing the focus state between the objective lens and the surface of the photomask and the objective position signal representing the position of the objective lens along its optical axis are also formed for each scan line. The scan length of each scan line is set to slightly exceed the length of the inspection area 30 in the X direction. Each scan line is respectively provided with one of consecutive numbers which are successively continued in the third direction from a scan start point to a scan end point, and each scan line is identified by the given consecutive number (that is, 1st, 2nd, 3rd, etc). That is, 1-th~n-th scan lines are set to cover an area slightly larger than the inspection area, each scan line is successively scanned and the entire inspection area is scanned when scanning action of the n-th scan line is completed. Furthermore, the 1-th and 2-th scan lines are set so as to be positioned outside of the inspection area.

The focus control signal for controlling the position of the objective lens along its optical axis is generated for each scan line by using the focus error signal of time series outputted from the light detection means 23 for each scan line and the objective position signal of time series outputted from the position sensor 10 for each scan line during the movement of the stage on each of the scan lines. During the movement of the stage, the position of the objective lens is automatically controlled in such a manner that the focal point of the objective lens is positioned on the surface of the photomask.

Figure 4:
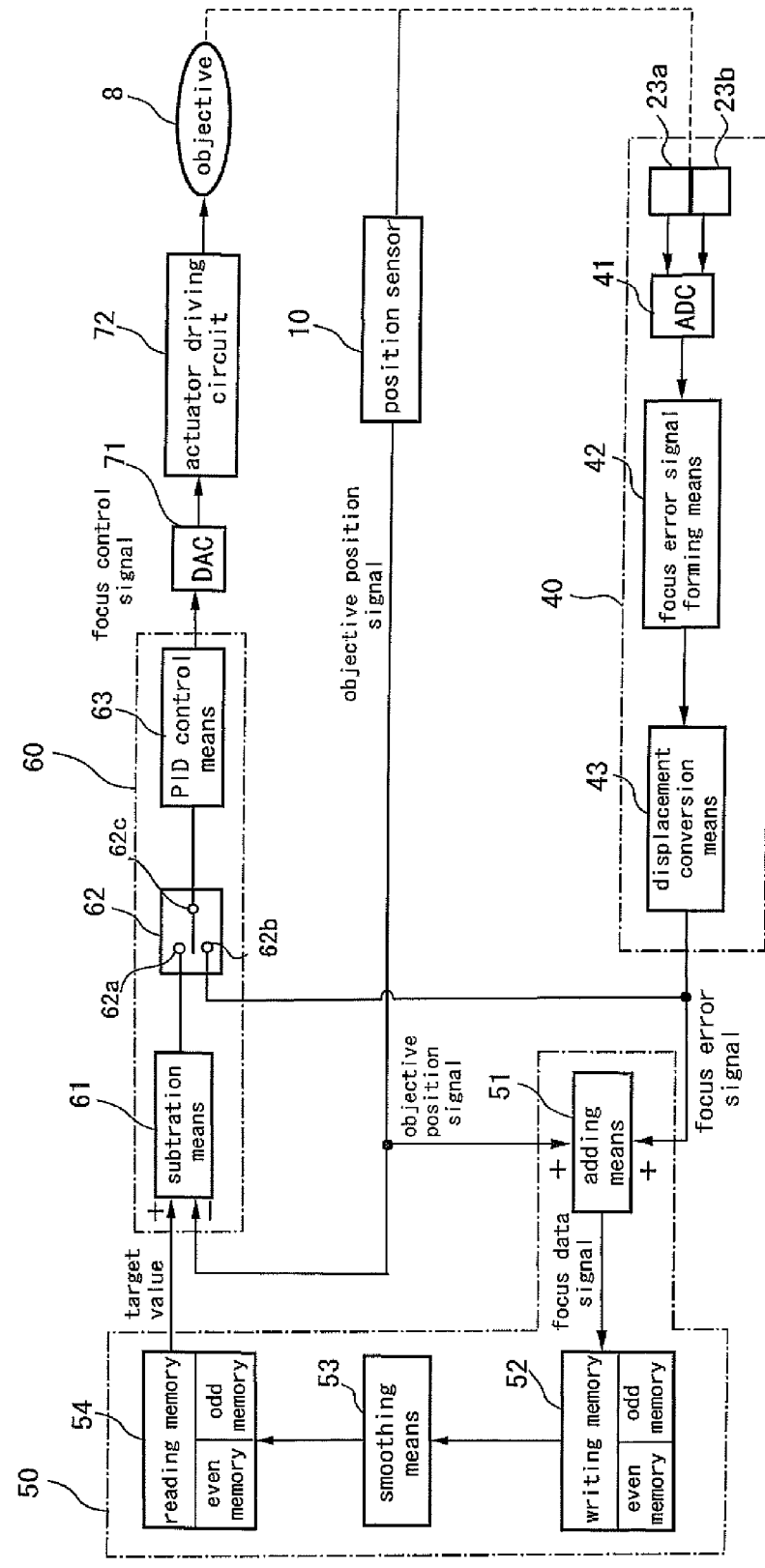
FIG. 4 is a view showing one example of a processor of an autofocus system.

Next, the autofocusing method according to the invention will be explained. FIG. 4 is a view showing one example of the processor 25 for generating the focus control signal. The processor 25 comprises focus error detection means 40 for generating the focus error signal representing the deviation between the focal point of the objective lens and the surface of the photomask, target value generation means 50 for generating a target value using a focus data signal comprising of the objective position signal or the objective position signal to which the focus error signal is added, and focus control signal generating means 60 for generating the focus control signal for controlling the position of the objective lens using the target value. In the present example, as the focus data signal which is used to produce the target value for scanning the (i+2)-th scan line, an addition value including the objective position signal and the focus error signal is used. Thereby, it is possible to complement the deviation occurred by the tracking delay of the objective lens by using the focus error signal.

The two photodiodes 23a and 23b of the light detector 23 which functions as a focus detector output focus signals Ia and Ib, respectively. These two focus signals are converted into digital signals by an A/D converter 41 and are supplied to focus error signal forming means 42. The focus error signal forming means 42 form a difference between the two focus signals (Ia-Ib) to produce a focus error signal of time series. The produced focus error signal represents the deviation along the optical axis between the focal point of the objective lens and the surface of the photomask. The formed focus error signal is supplied to displacement conversion means 43. The displacement conversion means 43 convert the focus error signal into a displacement along the optical axis of the objective lens. Therefore, the displacement conversion means 43 output the focus error signal which is converted into the displacement along the optical axis. Furthermore, Depending on a sign of the difference value (Ia-Ib), it is determined whether the objective lens should be moved in a direction closer toward or away from the substrate. The output signal from the displacement conversion means 43 is supplied to adding means 51 of the target value generation means 50. The adding means 51 have two inputs, one of which receives the focus error signal which is converted into a displacement.

The objective position signal of time series which is outputted from the position sensor 10 and represents the position of the objective lens along its optical axis is supplied to the other input of the adding means 51. The adding means 51 add the focus error signal to the objective position signal to output a focus data signal including the objective position signal and the focus error signal. Therefore, the focus data signal represents the best focus position of the objective during the scanning of the i-th scan line. Such focus data signal which represents the best focus position of the objective is stored in a writing memory 52 as data of time series and is to be used to generate the target values for scanning the (i+2)-th scan line.

The writing memory 52 comprises an even number memory for storing the focus data signal acquired when the scan line of even number being scanned and an odd number memory for storing the focus data signal acquired when the scan line of odd number being scanned. Then, the focus data signals are stored in the even number memory or the odd number memory alternately, depending on whether the number of the scanned scan line is even number or odd number.

The focus data signal which was acquired during the scanning period of the i-th scan line is temporarily stored in the writing memory 52 and then is supplied to smoothing means 53 in synchronization with the start of the scanning of the next (i+1)-th scan line. The smoothing means 53 perform the smoothing process for the inputted focus data signal and supply the smoothed focus data signal to a reading memory 54. The smoothed focus data signal is used as the target value for scanning the (i+2)-th scan line. As to the smoothing process, various smoothing processes can be used, and for example a moving average process can be performed. As another smoothing process, a low-pass filter processing can be used. In this case, it is possible that a cut-off frequency is determined based on a pattern density or a line width of the patterns formed on the photomask. Further, as another smoothing process, a difference value between the adjacent data of the focus data signal of time series is formed, and if the formed difference value exceeds given threshold, these data are removed from the focus data signal and a linear interpolation process is performed. Furthermore, since the smoothing process requires considerable processing time, the smoothing process for the focus data signal acquired during the scanning of the i-th scan line is performed during the scanning period of the next (i+1)-th scan line.

The reading memory 54 comprises an odd number memory and an even number memory, and the smoothed data signals are stored alternately in the even number memory or odd number memory depending on whether the number of scanned scan line is an even number or an odd number.

In synchronization with the start of the scanning of the (i+2)-th scan line, the target values for one scan line being temporally stored in the reading memory are serially supplied to one of inputs of subtraction means 61 of the focus control signal forming means 60. To the other input of the subtraction means 61, the objective position signals indicating the current position of the objective lens are serially supplied from the position sensor 10. The subtraction means 61 form a difference between the target value and the objective position signal so as to output a deviation signal representing the deviation between the target value and the current position of the objective lens.

Output signals from the subtraction means 61 are supplied to a first input 62a of a switch 62. A second input 62b of the switch 62 is connected to the output of the displacement conversion means 43. A common terminal 62c of the switch 62 is connected to PID control means 63 which functions as a compensator. The switch 62 is controlled so that during the scanning of the first two scan lines of the beginning of the inspection the common terminal 62c is connected to the second input terminal 62b and during the scanning of the scan lines after the third scan line the common terminal 62c is connected to the first input 62a. Therefore, while two scan lines positioned outside of the inspection area are scanned, the displacement which is outputted from the displacement conversion means 43 and corresponds to the focus error signal is supplied to the PID control means 63, and while the scan lines after the third are scanned, the deviation signal outputted from the subtraction means 61 is supplied to the PID control means 63.

The output signal from the subtraction means 61 passes through the switch 62 and is supplied to the PID control means 63. The PID control means 63 generate a PID control signal based on the deviation between the target value and the objective position signal indicating the current position of the objective lens and output the generated PID control signal as a focus control signal which controls the position of the objective lens along its optical axis. The PID control signal is converted into an analog signal by a D/A converter 71 and is supplied to an actuator driving circuit 72. The actuator driving circuit 72 generates a driving signal for driving the actuator 9 which drives the objective lens in its optical axis direction, and thereby the position of the objective lens along its optical axis is controlled. That is, the position of the objective along its optical axis is controlled so as to follow the target value.

In the present example, while the (i+2)-th scan line is scanned, the best focus position of the objective acquired during the scanning period of the i-th scan line which is two scan lines before is used as the target value. Therefore, the position of the objective lens is controlled by feedforward controlling using the deviation between such target value and the current position of the objective lens. In this case, since the focus error signal component included in the target value has been already smoothed by the smoothing means 53 and the objective position signal has little influence of the scattered light and the diffracted light, stable focus control without the influence of the scattered light and diffracted light emitted from the photomask is carried out.

Next, the autofocus operation according to the invention will be explained. As shown in FIG. 3, when the inspection starts, the stage starts to move in the first scan direction along the first scan line. At the same time, the second input 62b and the common terminal 62c of the switch 62 are switched so as to be connected to each other. Therefore, the displacement which is supplied from the displacement conversion means 43 and corresponds to the focus error signal is supplied to the PID control means 63, and thereby the position of the objective lens is controlled by the feedback control using the focus error signal. At the same time, the displacement or deviation corresponding to the focus error signal and the objective position signal are supplied to the adding means 51, and the addition output from the adding means is stored in the odd memory of the writing memory 52 as the focus data signal.

When the scanning of the first scan line is completed, the stage moves only a predetermined span length in the third direction, and then the stage starts to move in the second scan direction whose scan direction is opposite to that of the first direction along the second scan line. During the scanning of the second scan line, the switch 62 is kept in the same state and the position of the objective lens along its optical axis is controlled by the feedback control based on the deviation formed by using the focus error signal. When the scanning of the second scan line starts, the focus data signal stored in the writing memory is supplied to the smoothing means 53 and is smoothed. That is, the focus data signal is smoothed while the stage moves in the opposite scanning direction, and the smoothed focus data signal is sequentially stored in the odd number memory of the reading memory 54. In parallel with the smoothing process, the objective position signal and the displacement corresponding to the focus error signal are acquired and are supplied to the adding means 51, and then the addition output is sequentially stored in the even number memory of the writing memory 52 as the focus data signal of the second scan line.

When the scanning of the second scan line is completed, the switch 62 is switched such that the subtraction means 61 and the common terminal 62c of the switch are connected to each other. Then, the stage starts to move in the first direction along the third scan line. At the same time, the target values stored in the reading memory 54 are sequentially supplied to the subtraction means 61 and the objective position signals sequentially outputted from the position sensor 10 are also supplied to the subtraction means. Then, the PID control signals are formed based on the deviation between the target value and the current position of the objective lens so that the position of the objective lens along its optical axis is controlled so as to follow the target value. Further, the focus data signals stored in the writing memory 52 are supplied to the smoothing means 53 and are processed to be smoothed. And further, the addition outputs from the adding means 51 are stored in the odd number memory of the writing memory 52 sequentially. In this way, when the scanning of the final scan line is completed, the inspection of the photomask is completed.

Figure 5:
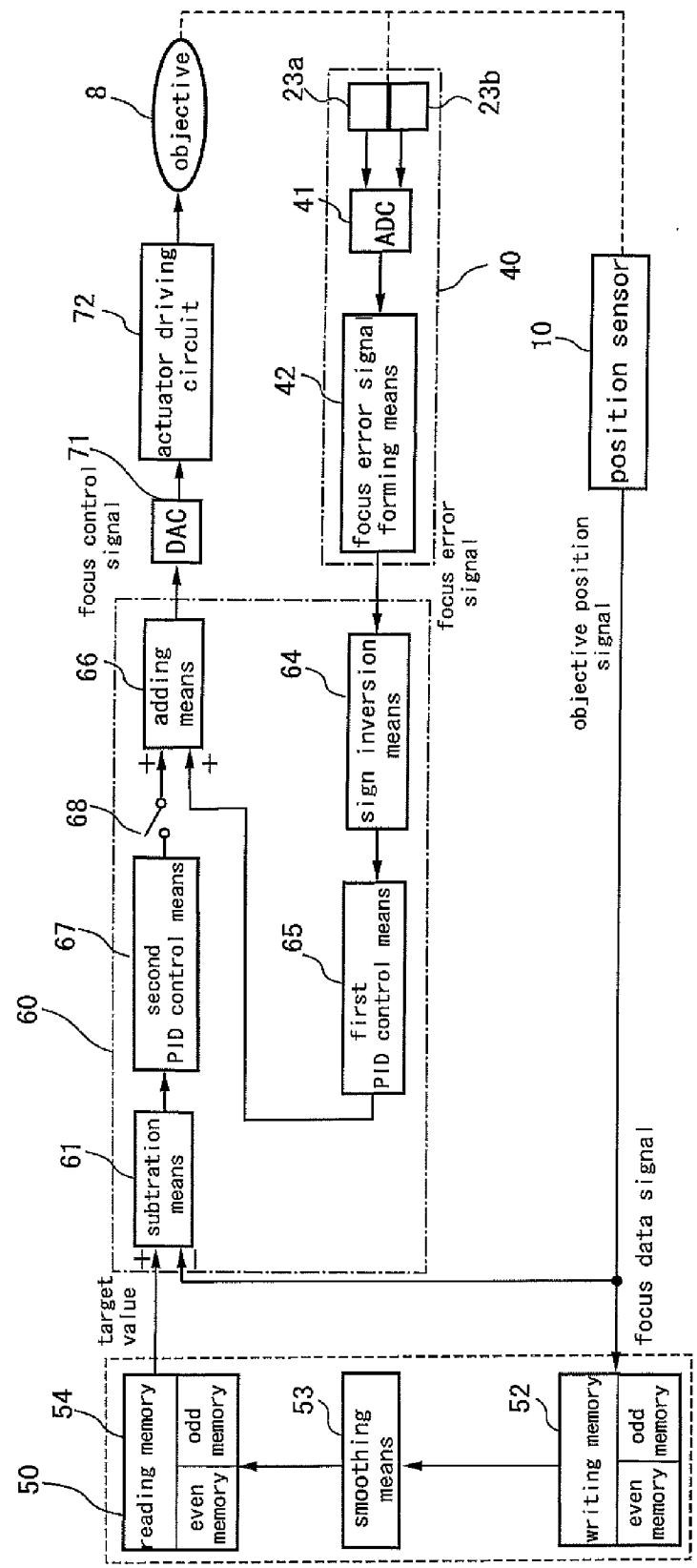
FIG. 5 is a view showing a modification of a processor.

FIG. 5 is a view showing a modification of the processor according to the invention. In the present example, the position of the objective lens along its optical axis is controlled by a hybrid type control in which a feedback control using the focus error signal and a feedback control using the objective position signal are combined. Further, component elements the same as the component elements which were used in FIG. 4 are assigned the same reference notations. The focus signals Ia and Ib of time series respectively outputted from the photodiodes 23a and 23b of the light detecting means 23 are converted into digital signals by A/D converter 41. These two focus signals are supplied to the focus error signal forming means 42 so as to form a focus error signal. The formed focus error signal is supplied to sign inversion means 64 so that the sign of the focus error signal is reversed. The focus error signal whose sign is reversed is supplied to first PID control means 65 so that the first PID control signal is formed based on the focus error signal. The first PID control signal is supplied to one of inputs of adding means 66.

In the present example, as a focus data signal the objective position signal representing the position of the objective lens is used. The objective position signals of time series which were detected during the scanning period of the i-th scan line are supplied to the writing memory 52 and stored as the focus data signal sequentially. These focus data signals are sequentially supplied to the smoothing means 53 in synchronization with the start of the scanning of the next (i+1)-th scan line and are smoothed. Then, the smoothed focus data signals are stored in the reading memory 54 and are used as a target value used for scanning the next (i+2)-th scan line.

The target value being stored in the reading memory 54 is supplied to the subtraction means 61 in synchronization with the start of the scanning of the next (i+2)-th scan line. To the subtraction means 61, the objective position signal which represents a current position of the objective lens is also supplied. Then, the deviation between the target value and the current position of the objective lens is formed and the formed deviation is supplied to second PID control means 67. The second PID control means 67 generate a second PID control signal based on the deviation between the smoothed objective position signal which was detected two scan lines before and the current position of the objective lens. This second PID control signal is supplied to adding means 66 through a switch 68. The switch 68 is kept open state during the scanning of the first two scan lines of the beginning and is switched to be closed after the second scan line.

At the adding means 66, the first PID control signal formed by using the focus error signal and the second PID control signal formed by using the objective position signal are added to each other to produce the focus control signal. The formed focus control signal is converted into an analog signal by a D/A converter 71 and is supplied to the actuator driving circuit 72. The actuator driving circuit 72 generates the driving signal for driving the actuator 9 which drives the objective lens along its optical axis in order to control the position of the objective 8 along the optical axis. That is, in the present example, the objective lens is controlled by the feedback systems based on the focus error signal and the objective position signal.

In the present example, during the scanning of the first two scan lines of the beginning, the inspection is not carried out and only the scanning for acquiring the target value is performed. In this scanning of the first two scan lines, the switch

68 is opened and the position of the objective lens is controlled by the feedback control using the focus error signal. In the scanning of the scan lines after the second scan line, the position of the objective lens is controlled by the feedback control using the objective position signal and the feedback control using the focus error signal together.

In the present example, it is desired that the first PID control means 65 (compensator) of the feedback control system based on the focus error signal is configured in such a manner that tracking of low frequency components is increased in order to make influence of the disturbance smaller. That is, the gain of the first PID control means 65 is adjusted so that the integral gain is increased and the differential gain is decreased. On the contrary, since the input signals to the second PID means 67 of the feedback system based on the objective position signal have already been smoothed and include a little noise component, the gain of the second PID control means is adjusted so that the PID control with high response to the high frequency component is carried out. In this way, according to the present example, two feedback systems having different gain characteristics are combined with each other, and thereby a hybrid type feedback control in which the tracking performance is complementarily complemented from the low frequency component to the high frequency component is realized.

Figure 6:
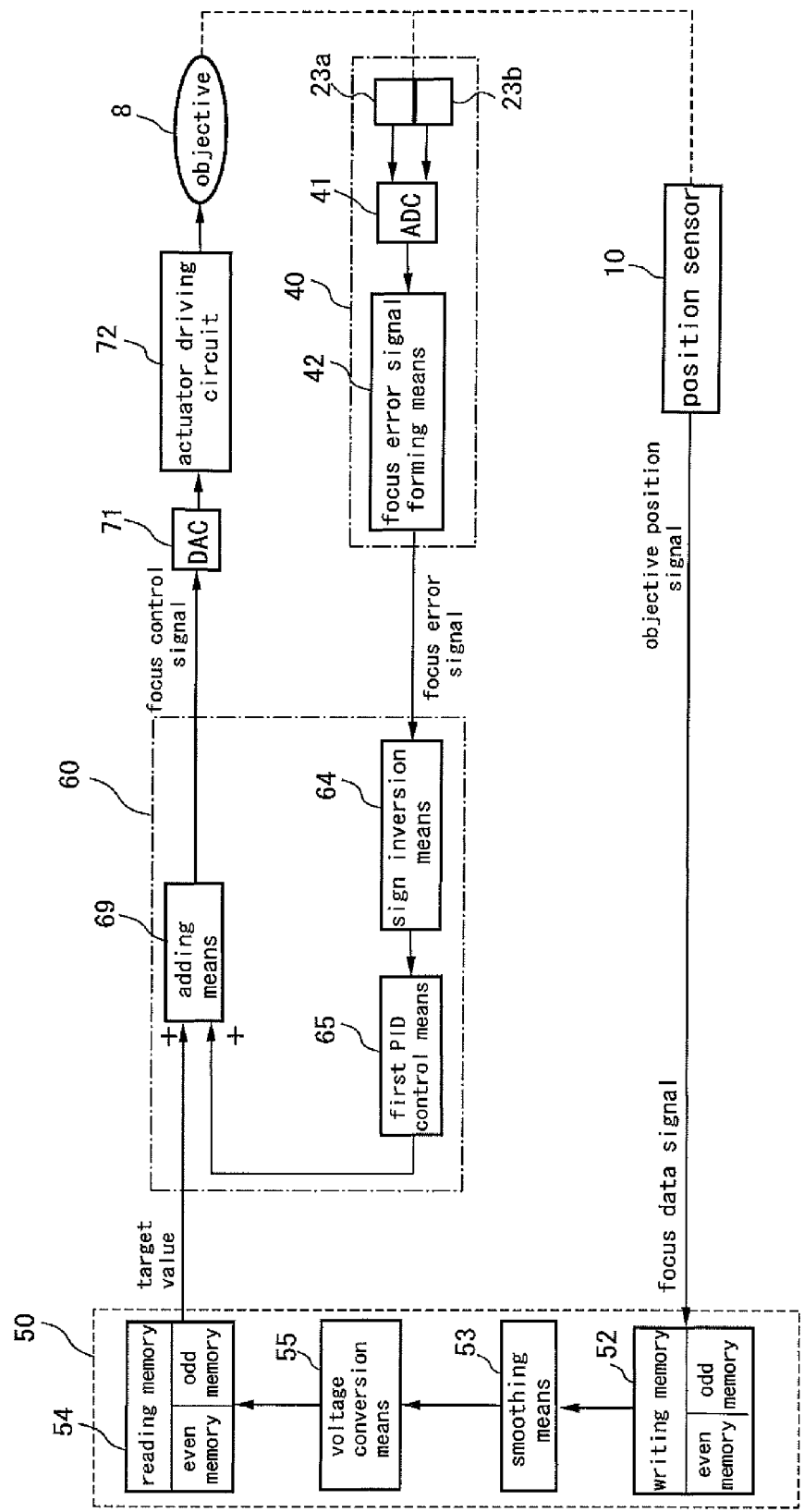
FIG. 6 is a view showing a modification of a processor according to the present invention.

FIG. 6 is a view showing another modification of the processor according to the invention. In the present example, the position of the objective lens along its optical axis is controlled by control system in which a feedback control using the focus error signal and a feedforward control using the objective position signal are combined. Further, component elements the same as the component elements which were used in FIG. 5 are assigned the same reference notations. In the present example, as the focus data signal which is used to generate a target value, the objective position signal outputted from the position sensor 10 is used. The focus signals Ia and Ib of time series respectively outputted from the photodiodes 23*a* and 23*b* of the light detecting means 23 are converted into digital signals by A/D converter 41. These two focus signals are supplied to the focus error signal forming means 42 so as to form a focus error signal. The formed focus error signal is supplied to sign inversion means 64 so that the sign of the focus error signal is reversed. The focus error signal whose sign is reversed is supplied to first PID control means 65 so that the first PID control signal is formed based on the focus error signal. The first PID control signal is supplied to one of the inputs of adding means 69.

Objective position signals which are detected during the scanning of the i-th scan line are supplied to the writing memory 52 and are sequentially stored as the focus data signal. The objective position signal stored in the writing memory is supplied to the smoothing means 53 in synchronization with the start of the scanning of (i+1)-th scan line and is smoothed. The smoothed objective position signal is to voltage conversion means 55 and is converted into a voltage value corresponding to the position of the objective. The converted voltage value is stored in the reading memory 54 and become target value which is used to scan the (i+2)-th scan line.

The voltage values of time series which are stored in the reading memory as the target values are sequentially supplied to the other input of the adding means 69 in synchronization with the start of the scanning of the (i+2)-th scan line. In the adding means 69, the first PID control signal formed by using the focus error signal and the target value formed by using the objective position signal are added to each other. Then, the addition output is converted into the analog signal by the D/A converter 71 and is supplied to the actuator driving circuit 72. The actuator driving circuit 72 generates the driving signal for driving the actuator 9 which drives the objective lens along its optical axis to control the position of the objective 8 along the optical axis.

In the present example, when the inspection is completed, the storage regions of the reading memory and the writing memory are made clear to zero. Therefore, since zero values are stored in the reading memory 54 during the scanning of the first two scan lines after the start of the inspection, the feedback control based on the focus error signal is carried out during the scanning of the first two scan lines after the start of the inspection and the objective position signals acquired during such scanning] period are stored in the writing memory sequentially. Thereafter, the processes which are similar to those performed in the embodiments shown FIG. 4 and FIG. 5.

In the present example, the position of the objective lens along its optical axis during the scanning is controlled by a control system in which the feedback control system based on the focus error signal and the feedforward control system based on the control voltage value (target value) which is formed from the objective position signal are combined. Therefore, in the present example, the feedback controlling using the focus error signal and the feedforward controlling using the objective position signal act complementarily. That is, in the feedback control using the focus error signal, noise components caused by the pattern diffracted light appear in the control signal and the tracking delay occurs as well. On the contrary, when the feedforward control is used together with the feedback control, an advantageous effect in which the drawback of the feedback control is complemented by the feedforward control is attained.

The present invention is not limited to the above-mentioned embodiments and can be modified and changed in various ways. For example, in the above-mentioned embodiments, the photomask was used as an object of the inspection, but it is possible to apply the present invention to various inspection apparatuses for inspecting for example a semiconductor substrate or a mask blanks.

Furthermore, in the above-mentioned embodiments, the stage which supports the substrate was made to move in a zigzag fashion, but it is possible to fix the stage in place and make the objective lens move in a zigzag fashion so as to scan the surface of the substrate, as worked in a large mask inspection apparatus for inspecting a large size photomask.

Furthermore, in the above-mentioned embodiments, the focus control signal which is used to scan the (i+2)-th scan line was produced using the objective position signal or objective position signal to which the focus error signal is added which was acquired during the scanning of the i-th scan line, but it is also possible to produce the focus control signal which is used to scan a (i+4)-th scan line, (i+6)-th scan line, or (i+2m)-th scan line (m being a natural number) by using the objective position signal or objective position signal to which the focus error signal is added which was acquired during the scanning of the i-th scan line. Because, the scanning direction of the (i+2m)-th scan line corresponds to that of the i-th scan line, and also the posture of the stage scanning of the (i+2m)-th scan line corresponds to the posture of the stage scanning of the i-th scan line.

Furthermore, in the above-mentioned embodiments, the explanation was given of position control of an objective lens used in an inspection apparatus in which a photomask is inspected, but the present invention is applicable to a focus control in various optical apparatus in which image data are acquired using an objective lens for focusing transmitted light through a sample or reflected light by the sample.

What is claimed is:

1. A substrate inspection apparatus comprising a stage for supporting a substrate to be inspected, an illumination optical system for projecting an illumination beam toward the substrate, an objective lens for focusing transmitted light through the substrate or reflected light by the substrate, light detection means for receiving the transmitted light or the reflected light emitted from the objective lens, a driving device for driving the objective lens along its optical axis, a position sensor for detecting a position of the objective lens along its optical axis to produce an objective position signal for representing the position of the objective lens along its optical axis, and an autofocus system for controlling the position of the objective lens along its optical axis during the inspection of the substrate, wherein:

said stage or the objective lens moves in a first scan direction, a second scan direction whose scanning direction is opposed to that of the first scan direction and a third direction which is perpendicular to the first and second scan directions in a zigzag fashion to scan on scan lines which respectively extend in the first or second scan direction and are set in the third direction one by one, and the inspection data for the substrate and the position data of the objective lens along its optical axis are acquired for each scan line during the scanning of respective scan lines, said autofocus system comprises focus error detection means for detecting a focus error between the objective lens and a surface of the substrate so as to generate a focus error signal, and focus control signal generation means for generating a focus control signal which is used to control the position of the objective lens along its optical axis using a focus data signal comprising of the objective position signal or the objective position signal to which the focus error signal is added, said autofocus system further comprises target value generation means for generating a target value which is used to form the focus control signal by use of the focus data signal, and said target value generation means comprises smoothing means for smoothing the focus data signal so as to output a smoothed focus data signal as the target value, when "i" is assumed as a positive integer and "m" is assumed as a natural number, the focus control signal which is used to scan an (i+2m)-th scan line is formed using the focus data signal which was acquired during the scanning period of an i-th scan line, and said focus control signal generation means generates the focus control signal using the target value which is formed for each scan line.

2. The apparatus of claim 1, wherein said natural number "m" is set to "1", and the focus data signal which was acquired in the scanning period of the i-th scan line is smoothed during the scanning period of a (i+1)-th scan line so that the smoothed focus data signal is outputted as the target value which is used for scanning the (i+2)-th scan line.

3. The apparatus of claim 2, wherein said focus data signal comprises of the objective position signal which is outputted from the position sensor.

4. The apparatus of claim 3, wherein said focus control signal generation means comprise first PID control signal generation means for forming a first PID control signal based on the focus error signal outputted from the focus error signal detection means, second PID control signal generation means for forming a second PID control signal based on a difference between the target value outputted from the second memory and the objective position signal supplied from the position sensor, and addition means for adding the first PID control signal to the second PID control signal to form the focus control signal.

5. The apparatus of claim 4, wherein the gain of the first PID control signal is adjusted so that the response in high frequency region is decreased and the gain of the second PID control signal is adjusted so that the response in high frequency region is increased.

6. The apparatus of claim 5, wherein the gain of the first PID signal is adjusted so that the integral gain is higher and the differential gain is lower.

7. The apparatus of claim 2, wherein said target value generation means comprises addition means for adding the focus error signal to the objective position signal, and wherein
said focus data signal includes the objective position signal which is outputted from the position sensor and the focus error signal which is converted to displacement along the optical axis.

8. The apparatus of claim 7, wherein said focus control signal generation means comprise subtraction means for forming a difference between the target value outputted from the second memory and the objective position signal supplied from the position sensor, and PID control signal generation means for forming the focus control signal based on the output signal from the subtraction means.

9. The apparatus of claim 2, wherein the target value generation means further comprises a first memory for storing the objective position signal or the objective position signal to which the focus error signal is added as the focus data signal and a second memory for storing the smoothed focus data signal, and wherein
the focus data signal which was acquired during the scanning period of the i-th scan line and stored in the first memory is smoothed during the scanning period of the (i+1)-th scan line, and the smoothed focus data signal is stored in the second memory, and the focus data signal stored in the second memory is outputted as the target value which is used to scan the (i+2)-th scan line.

10. The apparatus of claim 9, wherein the first and second memories comprise an odd number memory which stores the focus data signal which is acquired during the scan period of the scan line of odd number and an even number memory which stores the focus data signal which is acquired during the scan period of the scan line of even number, respectively.

11. The apparatus of claim 9, wherein said target value generation means include means for converting the smoothed objective position signal into a control voltage value, and the converted control voltage value is stored in the second memory as the target value, and wherein
said focus control signal generation means further include means for generating the PID control signal using the focus error signal and addition means for adding the generated PID control signal to the target value outputted from the second memory so that the focus control signal is outputted from the addition means.

12. The apparatus of claim 2, wherein said smoothing means perform a process of moving averages for the focus data signal.

13. The apparatus of claim 1, wherein said focus error signal detection means comprise a light source for projecting a light beam toward the substrate through the objective lens and light detection means for receiving the reflected light from the substrate through the objective lens, and wherein
the light detection means comprise first and second light detectors which are arranged along a direction in which the light spot formed on the light detection means moves in response to the focus error so that the focus error signal is formed based on the difference between the output signals from the first and second light detectors.

14. The apparatus of claim 1, wherein said focus error signal detection means comprise a light source for projecting a light beam toward the substrate through the objective lens and light detection means for receiving the reflected light from the substrate through the objective lens, and wherein the light detection means comprise a plurality of light receiving elements which are arranged along a direction in which the light spot formed on the light detection means moves in response to the focus error so that the focus error signal is formed based on the output signals from the light receiving elements.

15. The apparatus of claim 1, wherein the position of the objective lens along its optical axis is controlled by the feedback control which uses the focus error signal during the scanning of two scan lines of the beginning after the inspection starts.

16. The apparatus of claim 15, wherein the two scan lines of the beginning are positioned outside of an inspection area.

17. A mask inspection apparatus for detecting a defect existing on a photomask, the mask inspection apparatus comprising;

a stage for supporting a photomask to be inspected, an illumination system for projecting an illumination beam toward the photomask, an objective lens for focusing transmitted light through the photomask or reflected light by the photomask, a driving device for driving the objective lens along its optical axis, a position sensor for detecting the position of the objective lens along its optical axis to produce a objective position signal for representing the position of the objective lens along its optical axis, and an autofocus system for controlling the position of the objective lens along its optical axis during the inspection of the photomask, wherein:

said stage moves in a first scan direction, a second scan direction whose scanning direction is opposed to that of the first scan direction and a third direction perpendicular to the first and second scan directions in a zigzag fashion to scan on scan lines which respectively extend along the first or second direction and are set in the third direction one by one, and the inspection data for the photomask and the position data of the objective lens along its optical axis are acquired for each scan line during the scanning of respective scan lines, said autofocus system comprises focus error detection means for detecting a focus error between the objective lens and a surface of the substrate to generate a focus error signal, and focus control signal generation means for generating a focus control signal which is used to control the position of the objective lens using a focus data signal comprising of the objective position signal or the objective position signal to which the focus error signal is added, said autofocus system further comprises target value generation means for generating a target value which is used to form the focus control signal by use of the focus data signal, and said target value generation means comprises smoothing means for smoothing the focus data signal so as to output the smoothed focus data signal as the target value, when "i" is assumed as a positive integer and "m" is assumed as a natural number, the focus control signal which is used to scan an (i+2m)-th scan line is formed using the focus data signal which was acquired during the scanning period of an i-th scan line, and said focus control signal generation means generates the focus control signal using the target value which is formed for each scan line.

18. The mask inspection apparatus of claim 17, wherein said natural number "m" is set to 1, and the focus data signal which was acquired in the scanning period of the i-th scan line is smoothed during the scanning period of a (i+1)-th scan line so that the smoothed focus data signal is outputted as the target value which is used to scan the (i+2)-th scan line.

19. The mask inspection apparatus of claim 18, wherein the target value generation means further comprises a first memory for storing the focus data signal and a second memory for storing the smoothed focus data signal smoothed, and wherein the focus data signal which was acquired during the scanning period of the i-th scan line and stored in the first memory is smoothed during the scanning period of the (i+1)-th scan line, and the smoothed focus data signal is stored in the second memory, and the focus data signal stored in the second memory is outputted as the target value which is used to scan the (i+2)-th scan line.

20. The mask inspection apparatus of claim 19, wherein said target value generation means include addition means for adding the focus error signal to the objective position signal to produce the focus data signal, and the focus data signal including the position signal of the objective and the focus error signal is stored in the first memory.

21. A mask inspection apparatus for detecting a defect existing on a photomask, the mask inspection apparatus comprising;

a stage for supporting a photomask to be inspected, an illumination system for projecting an illumination beam toward the photomask, an objective lens for focusing transmitted light through the substrate or reflected light by the substrate, a driving device for driving the objective lens along its optical axis, a position sensor for detecting the position of the objective lens along its optical axis to produce a objective position signal for representing the position of the objective lens along its optical axis, and an autofocus system for controlling the position of the objective lens along its optical axis during the inspection of the photomask, wherein:

said stage moves in a first scan direction, a second scan direction whose scanning direction is opposed to that of the first scan direction and a third direction perpendicular to the first and second scan directions in a zigzag fashion to scan on scan lines which respectively extend along the first or second direction and are set in the third direction one by one, and the inspection data for the photomask and the position data of the objective lens along its optical axis are acquired for each scan line during the scanning of respective scan lines, said autofocus system comprises focus error detection means for detecting a focus error between the objective lens and the surface of the substrate to generate a focus error signal, addition means adding the focus error signal to the objective position signal so as to output the objective position signal to which the focus error signal is added as a focus data signal, and focus control signal generation means for generating a focus control signal which is used to control the position of the objective lens using the focus data signal, said autofocus system further comprises target value generation means for generating a target value which is used to form the focus control signal by use of the focus data signal, and said target value generation means comprises smoothing means for smoothing the focus data signal so as to output the smoothed focus data signal as the target value,
- when "i" is assumed as a positive integer and "m" is assumed as a natural number, the focus control signal which is used to scan an (i+2m)-th scan line is produced using the focus data signal which was acquired during the scanning period of an i-th scan line, and
- said focus control signal generation means generates the focus control signal using the target value which is formed for each scan line.

22. The mask inspection apparatus of claim 21, wherein said "m" is set to 1, and wherein
- the focus data signal which was acquired in the scanning period of a i-th scan line is smoothed during the scanning period of the (i+1)-th scan line, and the smoothed focus data signal is outputted as the target value which is used to scan the (i+2)-th scan line.

23. The mask inspection apparatus of claim 22, wherein the target value generation means further comprise a first memory for storing the focus data signal outputted from the addition means and a second memory for storing the smoothed focus data signal, and wherein
- the focus data signal which was acquired during the scanning period of the i-th scan line and stored in the first memory is smoothed in the next scanning period of the (i+1)-th scan line, and the smoothed focus data signal is stored in the second memory and is outputted as the target value which is to be used for scanning the (i+2)-th scan line.

24. The mask inspection apparatus of claim 23, wherein said smoothing means perform a process of moving averages for the focus data signal.

25. The mask inspection apparatus of claim 23, wherein said focus control signal generation means comprise subtraction means for forming a difference between the target value outputted from the second memory and the objective position signal supplied from the position sensor and PID control signal generation means for forming the focus control signal based on the output signal from the subtraction means.

26. The mask inspection apparatus of claim 21, wherein the position of the objective lens along its optical axis is controlled by the feedback control which uses the focus error signal during the scanning period of two scan lines of the beginning after the inspection starts.

27. The mask inspection apparatus of claim 26, wherein the two scan lines of the beginning are positioned outside of an inspection area.

* * * * *